United States Patent
Tsuda et al.

(10) Patent No.: US 6,661,241 B2
(45) Date of Patent: Dec. 9, 2003

(54) TEMPERATURE CONTROL FOR CONDUCTIVE MEMBER

(75) Inventors: Takao Tsuda, Nisshin (JP); Ken Naito, Nagoya (JP)

(73) Assignee: Nagoya Institute of Technology, Nagoya (JP)

(*) Notice: Subject to any disclaimer, the term of this patent is extended or adjusted under 35 U.S.C. 154(b) by 0 days.

(21) Appl. No.: 09/850,919

(22) Filed: May 7, 2001

(65) Prior Publication Data

US 2002/0017909 A1 Feb. 14, 2002

(30) Foreign Application Priority Data

May 8, 2000 (JP) ......................................... 2000-134088

(51) Int. Cl.[7] .............................................. G01R 27/08
(52) U.S. Cl. ...................................................... 324/713
(58) Field of Search ................................ 324/713, 639, 324/721; 73/23.41, 23.42, 23.36, 61.55, 61.59, 61.56; 702/24, 31

(56) References Cited

U.S. PATENT DOCUMENTS

| | | | |
|---|---|---|---|
| 5,005,399 A | * | 4/1991 | Holtzclaw et al. .......... 73/23.39 |
| 5,482,744 A | * | 1/1996 | Pearson ...................... 427/455 |
| 5,551,278 A | * | 9/1996 | Rounbehler et al. .......... 73/1 G |
| 5,551,283 A | * | 9/1996 | Manaka et al. ............. 73/31.01 |
| 5,778,681 A | | 7/1998 | Li et al. ....................... 62/50.2 |
| 5,954,860 A | * | 9/1999 | Gordon ........................... 95/87 |
| 6,190,613 B1 | * | 2/2001 | Watanabe et al. ............. 422/99 |

FOREIGN PATENT DOCUMENTS

GB      1178226      1/1970

OTHER PUBLICATIONS

EPO Office Letter/Search Report Jul. 20, 2001 EP 01 30 4062.

Fast Temperature Programming in Gas Chromatography using Resistive Heating; J. High Resol. Chromatogr 1999, 22. (8) 459–164; Wiley–Vch Verlag GmbH, D–69451 Weinheim 1999.

* cited by examiner

*Primary Examiner*—Safet Metjahic
*Assistant Examiner*—Etienne P LeRoux
(74) *Attorney, Agent, or Firm*—Abelman, Frayne & Schwab

(57) ABSTRACT

A device for controlling the temperature of a conductive member, which detects the electrical resistance of the conductive member, calculates the temperature of the conductive member based on the detected electric resistance, and adjusts the temperature of the conductive member based on the calculated temperature, is disclosed.

5 Claims, 3 Drawing Sheets

TEMPERATURE CONTROL FOR CONDUCTIVE MEMBER

BACKGROUND OF THE INVENTION

1. Field of the Invention

The present invention relates generally to a device for controlling the temperature of a conductive member, and to a gas chromatography system incorporating such a device.

2. Description of the Related Art

Temperature control is widely performed in many fields, such as gas chromatography. In gas sample chromatography, a system typically includes a section for cooling and collecting gas. The section collects rarefied sample gas in a trap tube by concentrating the sample gas, conveys the gas into a column at a relatively narrow zone, and separates the sample gas into its components. Such a gas chromatography system is widely used in the field of analysis or measurement of gas. It is desirable to collect sample gas in the trap tube and convey the trapped sample gas into the column accurately and rapidly. In order to accomplish this, accurate and rapid sensing and control of the temperature at the trap tube is required.

The trapping system for gas chromatograph conventionally measures the temperature of the trap tube only locally, however, because it senses the temperature with a sensor, such as a metal thermistor or a metal theromcouple close to the trap tube or with a direct joint of the trap tube. As a result, it is difficult to sense and control the temperature correctly.

Rapid temperature sensing is often difficult because of the comparatively large heat capacity of the temperature sensor itself and its fixture, and thus there is a delay in the thermal sensing. Such a delay is significant if the thermistor is jointed to the tube directly because the heat capacity at the joint of the thermistor and the tube becomes large. As a result, it is difficult to sense and control the temperature rapidly.

SUMMARY OF THE INVENTION

According to one aspect of the present invention, there is provided a device for controlling the temperature of a conductive member, comprising:

means for detecting the electric resistance of the conductive member;
means for calculating the temperature of the conductive member based on the electric resistance detected by means for detecting the electric resistance; and
means for adjusting the temperature of the conductive member based on the temperature calculated by means for calculating the temperature.

With the above-mentioned element according to the invention, the temperature of the conductive member such as a trap tube used for gas chromatograph is calculated using the detected electric resistance of the conductive member instead of detecting the temperature by the thermistor or the thermocouple. As a result, the mean temperature of the conductive member can be calculated, and thus it is possible to control the temperature of the conductive member correctly. Also, it is possible to control the temperature of the conductive member rapidly, because there is no delay resulting from the heat capacity of the conductive member.

The device according to the present invention can be applied to many fields including the gas chromatographic system.

Preferably, means for detecting the electric resistance comprises:

means for applying the pulse electric current with a predetermined pulse width to the conductive member at a predetermined time interval; and
means for detecting the voltage generated by applying the pulse electric current.

As the pulse current with the predetermined pulse is applied to the conductive member at the predetermined interval, unnecessary heating is avoided. Thus, as a heavy-current can be applied to the conductive member, it is possible to detect extremely small electric resistance at the order of $10^{-4}$ $\Omega$. Also, when the current is applied to the conductive member at the predetermined, e. g. a relatively short time interval, the voltage of the conductive member can be always detected while the pulse current is applied. Therefore, it is possible to control the temperature of the conductive member following the rapid temperature change. As a result, more accurate temperature control can be performed.

In this case, the electric resistance of the conductive member is determined by the detected voltage.

More preferably, means for adjusting the temperature comprises:

means for cooling the conductive member by spraying a coolant; and
means for heating the conductive member by applying the pulse electric current to the conductive member.

By such cooling and/or heating, it is possible to cool and/or heat the conductive member rapidly, and thus it is possible to control the temperature of the conductive member rapidly.

According to another aspect of the present invention, there is provided a gas chromatography system comprises a chromatograph, a trap tube for collecting gas to be supplied to the chromatograph, the trap tube consisting of a conductive material, and a device for controlling the temperature of the trap tube, comprising:

means for detecting the electric resistance of the conductive member such as the trap tube;
means for calculating the temperature of the conductive member based on the electric resistance detected by means for detecting the electric resistance; and
means for adjusting the temperature of the conductive member based on the temperature calculated by means for calculating the temperature.

With the above-mentioned element according to the invention, it is possible to control the trap tube accurately and rapidly, and thus a separation of trapped sample gas into components consisting of the sample gas can be performed at high accuracy.

According to one preferred embodiment, the trap tube is made from stainless steel.

In view of the foregoing, it is an object of the present invention to provide a device for controlling the temperature of the conductive member, e. g. a trap tube consisting of a conductive material correctly and rapidly.

It is another object of the present invention to provide a trapping system for a gas chromatograph comprising such a device.

BRIEF DESCRIPTION OF THE DRAWINGS

The present invention is described in detail below with reference to the accompanying drawings, wherein.

DETAILED DESCRIPTION OF PREFERRED EMBODIMENTS OF THE INVENTION

Figure 1:
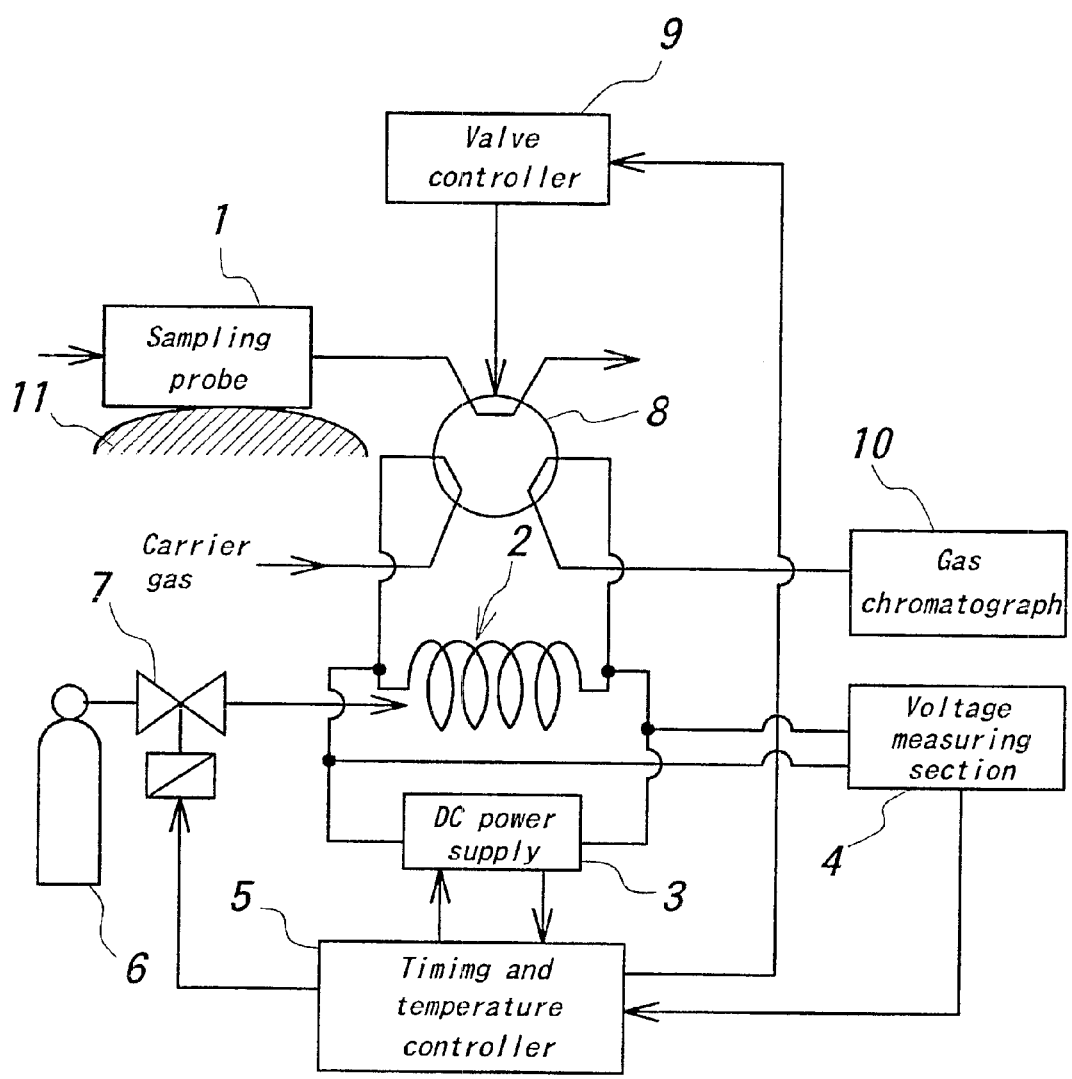
FIG. 1 is a schematic diagram showing embodiment of according to the present invention.

FIG. 1 is a schematic diagram showing embodiment of the device for controlling the temperature of the conductive member according to the present invention. In the embodiment, the device is applied to the trapping system for gas chromatograph and comprises a sampling probe 1, a metal trap tube 2, DC power supply 3, a voltage measuring section 4, a timing and temperature controller 5, a liquid carbon dioxide cylinder 6, solenoid valve 7, a six-way valve 8, a valve controller 9, and a gas chromatograph 10.

The sampling probe 1 for sample gas presents above a skin 11 of human continuously. A nitrogen gas system is passed through the sampling probe 1. The sample gas involved in the nitrogen gas stream is led into the trap tube 2. The trap tube 2 collects gas sampled by the sampling probe 1.

The DC power supply 3 applies a dc pulse to detect the temperature of the trap tube 2. The DC power supply 3 also supply the direct electric current to the trap tube 2, or apply the pulse current to the trap tube 2 to heat the trap tube 2. When detecting the temperature of the trap tube 2, for example, 5 A of the direct current is used and supplied for 6.5 msec of the duration per 100 msec as the dc pulse. The voltage measuring section 4 detects the voltage between terminals of the trap tube 2, the voltage being generated by the dc pulse.

The timing and temperature controller 5 is regulated by a CPU, for example. The timing and temperature controller 5 performs temperature control of the trap tube 2 based on a program stored in a memory such as a flush memory or a DRAM, or a recording medium such as an optical disk or a floppy disk. Thereby, the timing and temperature controller 5 calculates the mean temperature of the trap tube 2 based on the current supplied from the DC power supply 3, or the signal supplied from the voltage measuring section 4.

If a stainless steel tube with 0.8 mm of the internal diameter and 20 cm of the length is used as the trap tube 2 and 5 A of the dc pulse electric current is applied to the trap tube 2 when sensing the temperature of the trap tube 2, the following relation exists.

$$R = 1.445 \times 10^{-4} T + 0.509$$

$$V = 7.27 \times 10^{-4} T + 0.255$$

In this case, R, V and T represent the electric resistance ($\Omega$), the voltage (V) and the temperature (° C) of the stainless steel tube, respectively.

For example, If the temperature is 75° C., the electric resistance is 0.040 $\Omega$, and if the temperature is 90° C., the electric resistance is 0.064 $\Omega$. As the trap tube 2 itself is very conductive and short, the electric resistance observed is extremely low at the order of $10^{-4}$ $\Omega$.

The timing and temperature controller 5 also supplies the signal having the information whether the trap tube 2 should be heated or not to the DC power supply 3 based on the temperature obtained as a result of the calculation, supplies the signal having the information whether the solenoid valve 7 should be opened or closed or not to the solenoid valve 7, and supplies the signal having the information as to the open and close of a certain line of the six-way valve to the valve controller 9 which is composed of a CPU, for example.

The cylinder 6 is filled with the coolant consisting of liquid $CO_2$ gas or the mixture of liquid nitrogen and gas. The coolant is sprayed to the trap tube 2 and cools the trap tube 2 when the solenoid valve 7 is opened.

A certain line of the six-way valve 8 is opened and closed by the valve controller 9 based on the signal from the timing and temperature controller 5. Therefore, the switching of the passage by the six-way valve 8 is performed, the sample gas is led and trapped into the trap tube 2. The trapped sample gas is released by heating and led into a capillary column (not shown) in the gas chromatograph 10.

If the gas chromatograph is performed using the device shown in FIG. 1, first, the trap tube 2 is heated in advance, and thus cleaned so that similar chemical substrates as the sample gas does not exist in the trap tube 2. Subsequently, the trap tube 2 is cooled, and the sampling gas is led and trapped into the trap tube 2. The trap tube 2 is heated rapidly to the preferable temperature for the desorption of the trapped sample gas e.g. 90° C. at the rapid heating rate of 20° C. per second, for example, and thus the desorption of the trapped sample gas is performed. The desorbed and trapped sample gas is led into the capillary column (not shown) in the gas chromatograph 10, and separated into components of the sampling gas.

The operation of this embodiment is now described in detail.

When the DC power supply 3 applies the pulse current for sensing the temperature to the trap tube 2, the signal having information as to the voltage of the trap tube 2 is supplied to the timing and temperature controller 5. The timing and temperature controller 5 calculates the mean temperature of the trap tube 2 based on the signal, it is determined whether the trap tube 2 should be cooled or heated based on the calculated temperature.

If it is determined that the trap tube 2 should be heated, the timing and temperature controller 5 supplies the signal having an instruction which performs the heating of the trap tube 2 to the DC power supply 3. The DC power supply 3 applies the pulse current for heating to the trap tube 2 based on the signal. On the other hand, if it is determined that the trap tube 2 should be cooled, the timing and temperature controller 5 supplies the signal having an instruction which performs the cooling of the trap tube 2 to the solenoid valve 7. The solenoid valve 7 is opened based on the signal.

According to the embodiment, it is possible to control the trap tube 2 accurately and rapidly. As a result, it is possible to separate the sampling gas into components of the sampling gas at high accuracy.

Figure 2:
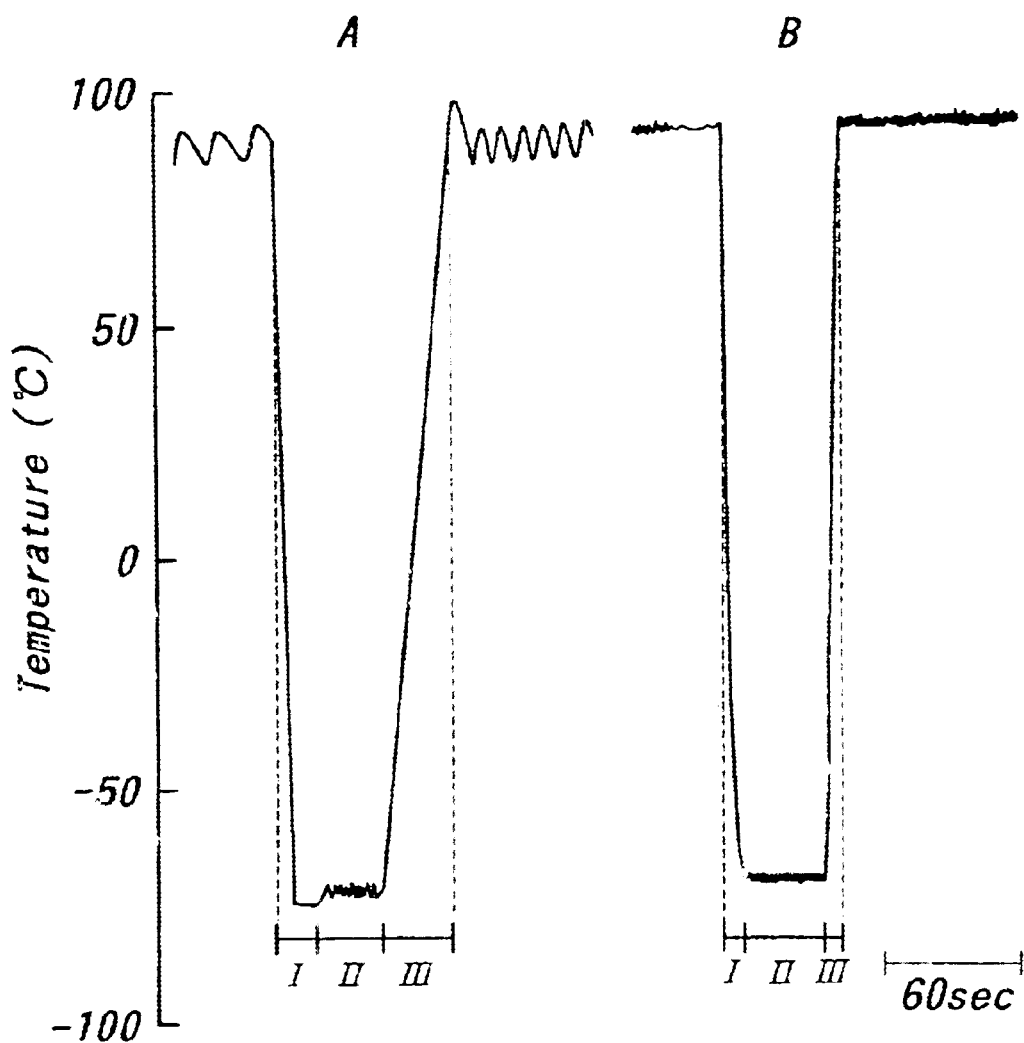
FIG. 2A is a temperature-time curve explaining a temperature control according to the prior art.
FIG. 2B is a temperature-time curve explaining a temperature control according to the present invention.

FIG. 2A is a temperature-time curve explaining a temperature control according to the prior art, and FIG. 2B is a temperature-time curve explaining a temperature control according to the present invention. In both cases, time is shown in horizontal direction, the temperature is shown in vertical direction. I represents the period from the beginning of the cooling to the end of the cooling, II represents the period from the end of the cooling to the beginning of the heating, and III represents the period from the beginning of the heating to the end of the heating. The setting temperature of the cooling is −70° C. and the setting temperature of the heating is 90° C. in both cases.

As shown in FIG. 2A, the temperature reaches below the setting temperature of the cooling in period I, therefore, the temperature does not reach the setting temperature accurately. Also, the temperature reaches above the setting temperature of the heating after period III, therefore, the temperature does not reach the setting temperature accurately. As a result, the temperature is not controlled accurately. Moreover, both period I and period III are relatively long, therefore, the temperature is not controlled rapidly.

On the other hand, as shown in FIG. 2B, the temperature reaches the setting temperature of cooling at the ends of period I and period III accurately. As a result, accurate temperature control is realized. Also, period I is not more than half of that shown in FIG. 2A, and period III is not more than half of that shown in FIG. 2A, too. Therefore, the rapid temperature control is realized. Moreover, the temperature is sensed accurately and rapidly before period I, in periods I–III, and after period III.

Figure 3:
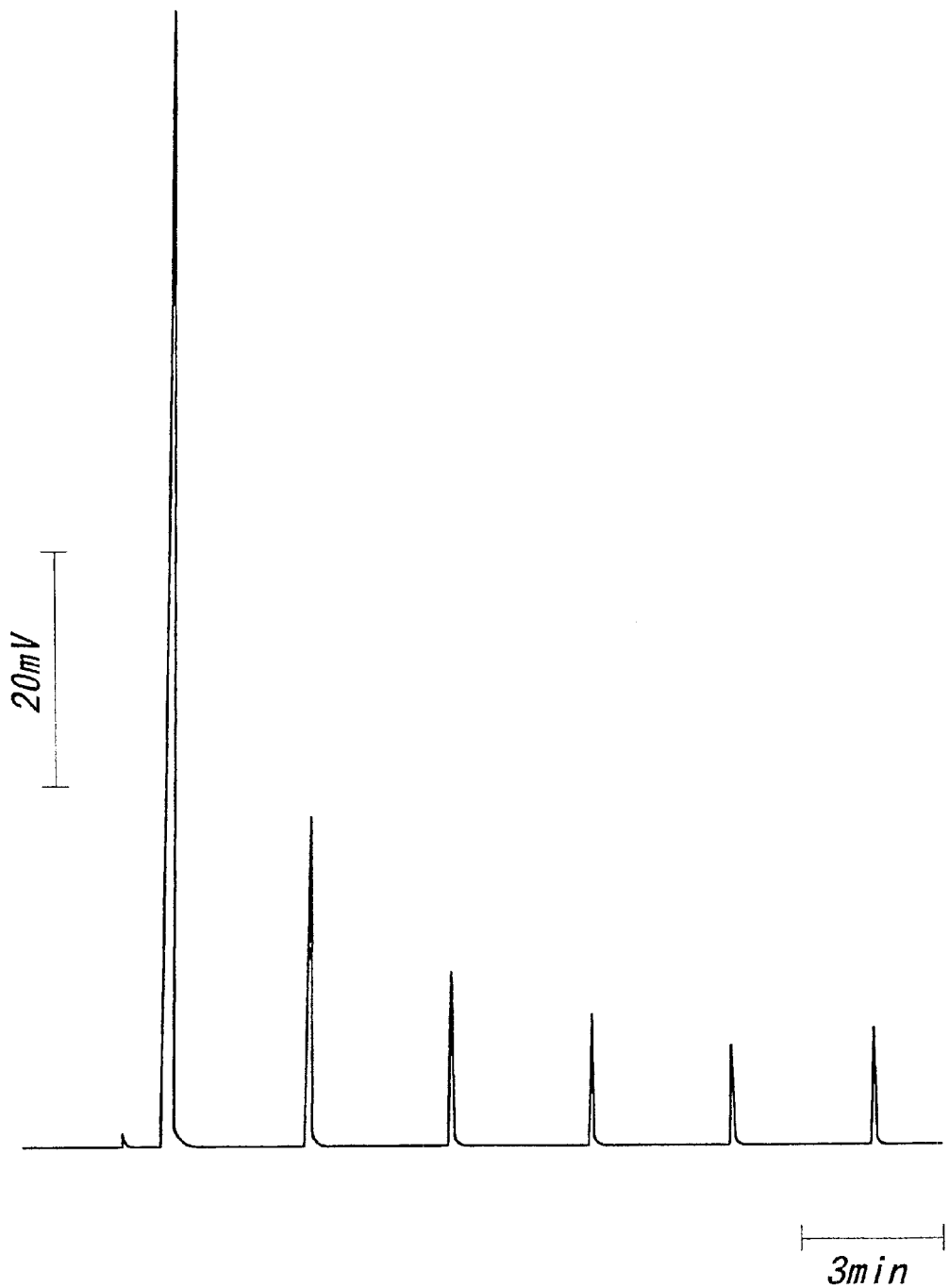
FIG. 3 is a graph showing an analyzing result obtained by the present invention.

FIG. 3 is a graph showing an analyzing result obtained by the present invention. It shows the process of the releasing of ethyl alcohol from the surface of a skin of human. In this example, after a thumb of human is dipped into 10% aqueous solution of ethyl alcohol for 1 minute, skin of the thumb is sampled with a sampling probe per 3 minutes, and the releasing quantity of ethyl alcohol from the skin of the thumb is measured repeatedly. As shown in FIG. 3, each of peaks of the gas chromatograph is very sharp, and thus components of trapped sample gas is separated at high accuracy.

While the present invention has been described above with reference to certain preferred embodiments, it should be noted that it were presented by way of examples only and various changes and/or modifications may be made without departing from the scope of the invention. For example, the device according to the present invention can be applied to any other field than the gas chromatograph. The metal trap tube is used as the conductive member, however, any other kind of the conductive member can be used. The above mentioned embodiment can be applied when the sensing of the temperature is only performed. Moreover, it is preferable to determine the pulse width and the interval of the pulse current in accordance with the property of the conductive member and the necessary speed of control.

What is claimed is:

1. A device for controlling the temperature of a conductive member comprising:

means for detecting the value of the electrical resistance of the conductive member on the order of $10^{-4}$ ohms utilizing a pulse current having a predetermined pulse width;

means for calculating the temperature of the conductive member based on the electrical resistance detected by the means for detecting the electrical resistance; and means for adjusting the temperature of the conductive member based on the temperature calculated by the means for calculating the temperature.

2. The device according to claim 1, wherein the means for detecting the electrical resistance comprises:

means for applying the pulse electric current to the conductive member at a predetermined time interval; and means for detecting the voltage generated by applying the pulse electric current.

3. The device according to claim 1, wherein the means for adjusting the temperature comprises:

means for cooling the conductive member by spraying a coolant; and means for heating the conductive member by applying the pulse electric current to the conductive member.

4. A gas chromatographic system comprises:

a gas chromatograph, a trap tube for sampling gas to be supplied to the chromatograph, the trap tube being made of a conductive material, and a device for controlling the temperature of the trap tube including:

means for detecting the electrical resistance of the conductive member on the order of $10^{-4}$ ohms utilizing a pulse current having a predetermined pulse width;

means for calculating the temperature of the conductive member based on the electrical resistance detected by the means for detecting the electrical resistance; and means for adjusting the temperature of the conductive member based on the temperature calculated by the means for calculating the temperature.

5. The gas chromatograph system of claim 4 wherein the trap tube is made from stainless steel.

* * * * *